United States Patent [19]
Jones

[11] 4,072,467
[45] Feb. 7, 1978

[54] COMBUSTIBLE GAS DETECTORS

[75] Inventor: Eric Jones, Chelmsford, England

[73] Assignee: English Electric Valve Co., Ltd., England

[21] Appl. No.: 732,861

[22] Filed: Oct. 15, 1976

[30] Foreign Application Priority Data

June 18, 1976 United Kingdom ............. 25464/76

[51] Int. Cl.² ........................................... G01N 27/16
[52] U.S. Cl. ........................................ 23/254 E; 338/34
[58] Field of Search ..................... 23/254 E, 232 E; 338/34; 340/237 R; 73/23, 27 R

[56] References Cited

U.S. PATENT DOCUMENTS

| | | | |
|---|---|---|---|
| 2,904,406 | 9/1959 | Moore | 23/254 E X |
| 3,586,486 | 6/1971 | Kim et al. | 23/254 E |
| 3,883,307 | 5/1975 | Kim | 23/254 E |

FOREIGN PATENT DOCUMENTS

1,387,412  3/1975  United Kingdom ............. 23/254 E

*Primary Examiner*—Robert M. Reese
*Attorney, Agent, or Firm*—Diller, Brown, Ramik & Wight

[57] ABSTRACT

A gas detector consists of a heatable wire filament which exhibits a change in resistance when its temperature rises due to the oxidization of a combustible gas pouring over it. The filament is embedded in a pellet consisting of a homogeneous mixture of an oxidization catalyst material and a substantially non-catalytic carrier material. A layer of the oxidization catalyst material is produced on the outside of the pellet.

9 Claims, 1 Drawing Figure

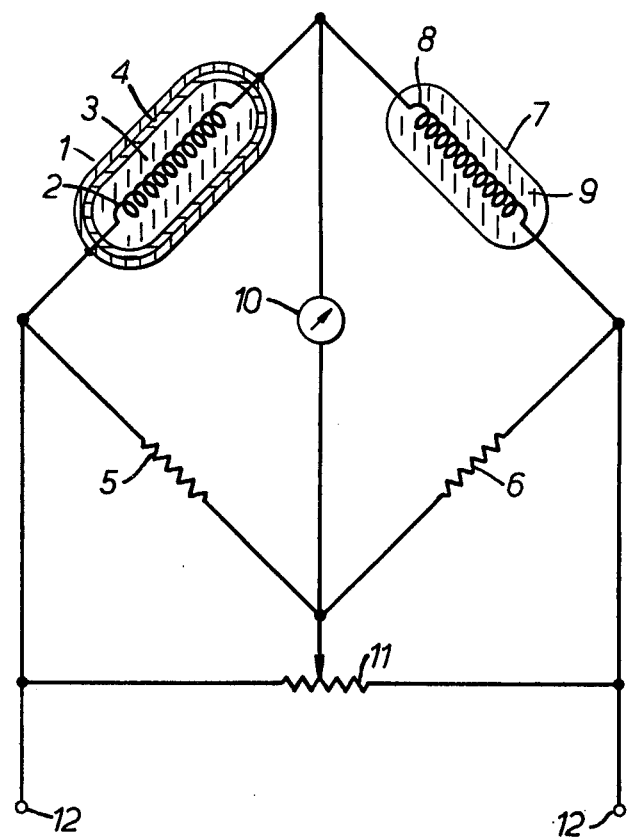

COMBUSTIBLE GAS DETECTORS

This invention, like that which is the subject of our United Kingdom Pat. No. 1,387,412, relates to combustible gas detectors and more particularly to combustible gas detectors of the kind in which a heatable wire filament exhibits a change in resistance occasioned by the change in its temperature which occurs due to the oxidisation of a combustible gas passing over it. Such gas detectors are usually included in a bridge circuit, the change in the balance of which as the resistance of the wire filament changes being utilised to provide an indication of the concentration of the combustible gas.

Whilst it is possible to use a naked wire filament it is also common to use a wire filament which is embedded in a pellet of ceramic material to provide a more rugged structure. It is also common to coat such a pellet with an oxidisation catalyst which reduces the temperature at which oxidisation of the combustible gas takes place, in order to reduce or prevent evaporation of the wire filament so as to reduce any tendency for the characteristics of the gas detector to change in service.

A gas detector as described above suffers from the disadvantage that the manufacturing process is a relatively involved one. In order to provide the pellet of ceramic material it is usual to immerse the wire filament in a solution of material which, when heated, decomposes to ceramic material, remove the liquid, heat the filament in order to dry out the solution adhering to the filament and repeat the process for as many times as is necessary to obtain the desired thickness of ceramic material forming the pellet. A similar process is then required to be repeated to form the layer of catalyst material on the pellet.

It is believed that there is a tendency for the gas detector to suffer from a change in its characteristic over a prolonged period due to the tendency for one material partially to diffuse into the other.

In accordance with the invention which is the subject of United Kingdom Pat. No. 1,387,412 a gas detector of the kind referred to is provided wherein said heatable wire filament is of platinum and is embedded in a pellet consisting of a homogeneous mixture of an oxidisation catalyst material and a substantially non catalytic carrier material.

The present invention seeks to provide a combustible gas detector generally in accordance with the invention in our United Kingdom Pat. No. 1,387,412 which is of improved long term stability.

According to this invention a gas detector of the kind referred to is provided wherein said heatable wire filament is embedded in a pellet consisting of a homogeneous mixture of an oxidisation catalyst material and a substantially non catalytic carrier material and a layer of oxidisation catalyst material is provided on the outside of said homogeneous pellet. Preferably said layer completely surrounds said pellet.

Preferably said catalyst material of said homogeneous mixture forming said pellet and said catalyst material of said layer are both palladium and/or platinum.

Preferably again said carrier material is alumina.

As is well known, it is usual to include in the balanced bridge circuit in one arm of which the gas detector is included, a compensating element which is similar to the gas detector save for the fact that no catalyst material is provided and the refractory material is poisoned to suppress the oxidisation of combustible gases. The function of the compensating element is to compensate for changes in ambient conditions, its value of resistance being sensitive only to changes in ambient conditions.

In balanced bridge circuit arrangements, including a gas detector in accordance with the present invention, as described above, a compensating element is provided which consists of a wire filament embedded in a pellet consisting of a homogeneous mixture of a substantially non catalytic carrier material and a poison acting to suppress the oxidisation of combustible gases. Preferably said poison is potassium hydroxide. Preferably the wire filament of said detector and said compensating element is of platinum.

The invention is illustrated in and further described with reference to the accompanying drawing which illustrates a balanced bridge arrangement including a gas detector in accordance with the present invention for use in the detection of combustible gases.

Referring to the drawing, 1 is a gas detector consisting of a heatable wire filament 2 of platinum embedded in a pellet 3 consisting of a homogeneous mixture of alumina, and an oxidisation catalyst material, palladium and platinum. Surrounding, completely in this example, the pellet 3 is a layer 4 of oxidisation catalyst material. In this example the oxidisation catalyst material of the layer 4 is also a mixture of palladium and platinum formed by applying relatively high concentration solutions to the outside of the pellet 3.

The gas detector 1 is included in one arm of a balanced bridge arrangement consisting of resistors 5 and 6 of equal value and a compensating element 7. The compensating element 7 consists of a wire filament 8 of platinum embedded in a pellet 9 consisting of a homogeneous mixture of alumina, and a poison, potassium hydroxide, adapted to inhibit the oxidisation of combustible gases. Across the bridge is connected a voltmeter 10, calibrated to indicate combustible gas concentrations. The meter 10 is arranged to be set to zero by the adjustment of the slider on a potentiometer 11. Terminals 12 are provided to be connected to a source of power providing both the heating current for the filaments 2 and 8 and voltage for the bridge.

Except for the nature of the gas detector 1, the arrangement is, in fact, as known per se.

In operation the gas detector 1 and compensating element 7 are exposed to normal atmosphere and the slider potentiometer 11, adjusted to give a zero reading on meter 10. The gas detector 1 and compensating element 7 are then exposed to the atmosphere which it is required to monitor. Any combustible gases in the atmosphere oxidise on the surface of gas detector 1 but not on the surface of compensating element 7, causing the temperature of the filament 2 to rise with a consequent change in its resistance. The reading meter 10 then provides a measure of concentration of combustible gases in the atmosphere.

In the manufacture of the gas detector 1, the filament 2 is first wound and then cleaned. A solution of palladium chloride, platinum chloride, concentrated hydrochloric acid, distilled water and an aluminum nitrate solution is then made up in the following quantities:

1 gram of palladium chloride
1 gram of platinum chloride
12.5 ml of concentrated hydrochloric acid
12.5 ml of distilled water
100 ml of saturated aluminum nitrate solution at 20° C.

A pellet is then built up upon the platinum filament 2 by an evaporation technique as known per se.

A solution of palladium chloride, platinum chloride, concentrated hydrochloric acid, distilled water and an aluminium nitrate solution is then made up in the following quantities:

1 gram of palladium chloride
1 gram of platinum chloride
25 ml 2.5N concentrated hydrochloric acid
3 ml saturated aluminium nitrate solution at 20° C.

Using this solution a layer is then formed around the pellet previously formed, again by an evaporation technique. The compensating element 6 is also formed by an evaporation technique in a manner similar to that in which the basic pellet of the gas detector is formed except that potassium hydroxide replaces the chlorides in the solution.

As with known gas detector elements, prior to operation the element is "activated" by operating the element at elevated temperature in a reducing atmosphere.

With the constituents above mentioned used for the detector element and compensatory element, the former naturally is dark in colour whilst the latter is light in colour. Thus the former has a thermal emissivity which is different from that of the latter. This leads to a change in the balance of the bridge upon a change of voltage applied to terminals 12. In order to minimise this, a compensating resistor (not shown) may be connected across the compensating element 7.

I claim:

1. A gas detector of the kind in which a heatable wire filament exhibits a change in resistance occasioned by the change in its temperature which occurs due to the oxidisation of a combustible gas passing over it and wherein said heatable wire filament is embedded in a pellet consisting of a homogeneous mixture of an oxidisation catalyst material and a substantially non catalytic carrier material and a layer of oxidisation catalyst material is provided on the outside of said homogeneous pellet.

2. A gas detector as claimed in claim 1 and wherein said layer completely surrounds said pellet.

3. A gas detector as claimed in claim 1 and wherein said catalyst material of said homogeneous mixture forming said pellet and said catalyst material of said layer are both palladium.

4. A gas detector as claimed in claim 1 and wherein said catalyst material of said homogeneous mixture forming said pellet and said catalyst material of said layer are both platinum.

5. A gas detector as claimed in claim 1 and wherein said catalyst material of said homogeneous mixture forming said pellet and said catalyst material of said layer are both palladium and platinum.

6. A gas detector as claim in claim 1 and wherein said carrier material is alumina.

7. A balanced bridge circuit arrangement including a gas detector as claimed in claim 1 and wherein a compensating element is included which consists of a wire filament embedded in a pellet consisting of a homogeneous mixture of a substantially non catalytic carrier material and a poison acting to suppress the oxidisation of combustible gases.

8. A balanced bridge circuit arrangement as claimed in claim 7 and wherein said poison is potassium hydroxide.

9. A balanced bridge circuit arrangement as claimed in claim 7 and wherein the wire filament of said detector and said compensating element is of platinum.

* * * * *